(12) United States Patent
Kerr

(10) Patent No.: US 7,056,329 B2
(45) Date of Patent: Jun. 6, 2006

(54) LAPAROSCOPIC DIRECT VISION DISSECTING PORT

(75) Inventor: Stephen Kerr, Sunset Beach, CA (US)

(73) Assignee: Intellimed Surgical Solutions, LLC, San Juan Capistrano, CA (US)

( * ) Notice: Subject to any disclaimer, the term of this patent is extended or adjusted under 35 U.S.C. 154(b) by 503 days.

(21) Appl. No.: 10/278,572

(22) Filed: Oct. 23, 2002

(65) Prior Publication Data

US 2004/0082969 A1   Apr. 29, 2004

(51) Int. Cl.
*A61B 17/28* (2006.01)
(52) U.S. Cl. .................................. 606/206; 606/190
(58) Field of Classification Search ............. 606/181, 606/185, 184, 190, 198, 1, 174
See application file for complete search history.

(56) References Cited

U.S. PATENT DOCUMENTS

| | | | |
|---|---|---|---|
| 5,020,514 A | 6/1991 | Heckele | 128/4 |
| 5,098,388 A | 3/1992 | Kulkaski et al. | 604/158 |
| 5,104,394 A | 4/1992 | Knoepfler | 606/143 |
| 5,256,149 A | 10/1993 | Banik et al. | 604/164 |
| 5,282,807 A | 2/1994 | Knoepfler | 606/143 |
| 5,354,302 A | 10/1994 | Ko | |
| 5,373,840 A | 12/1994 | Knighton | 128/4 |
| 5,385,572 A | 1/1995 | Nobles et al. | 606/185 |
| 5,431,151 A | 7/1995 | Riek et al. | 600/164 |
| 5,441,041 A | 8/1995 | Sauer et al. | 600/106 |
| 5,447,513 A | 9/1995 | Davison et al. | 606/143 |
| 5,551,947 A | 9/1996 | Kaali | 604/264 |
| 5,569,291 A | 10/1996 | Privitera et al. | 606/185 |
| 5,569,292 A | 10/1996 | Schwemberger et al. | 606/185 |
| 5,591,192 A | 1/1997 | Privitera et al. | 606/185 |
| 5,609,562 A | 3/1997 | Kaali | 600/114 |
| 5,632,717 A | 5/1997 | Yoon | 600/106 |
| 5,653,726 A | 8/1997 | Kieturakis | 606/190 |
| 5,667,478 A | 9/1997 | McFarlin et al. | 600/182 |
| 5,676,682 A | 10/1997 | Yoon | 606/185 |
| 5,720,761 A | 2/1998 | Kaali | 606/185 |
| 5,738,628 A | 4/1998 | Sierocuk et al. | 600/104 |
| 5,797,906 A | 8/1998 | Makower et al. | |
| 5,860,996 A | 1/1999 | Urban et al. | 606/185 |
| 5,984,919 A | 11/1999 | Hilal et al. | |
| 6,042,596 A * | 3/2000 | Bonutti | 606/190 |
| 6,206,823 B1 | 3/2001 | Kolata et al. | 600/129 |
| 6,228,097 B1 | 5/2001 | Levinson et al. | 606/142 |
| 6,436,119 B1 * | 8/2002 | Erb et al. | 606/185 |

FOREIGN PATENT DOCUMENTS

| | | |
|---|---|---|
| DE | 10037421 A | 5/2002 |
| EP | 1036544 A | 9/2000 |
| WO | WO 8303189 A | 9/1983 |

* cited by examiner

Primary Examiner—Kevin T. Truong
(74) Attorney, Agent, or Firm—Raymond A. Miller; Pepper Hamilton LLP

(57) ABSTRACT

A laparoscopic direct vision dissecting port for providing safe entry into a body cavity, as well as being operative to serve as a standard laparoscopic port for use in laparoscopic surgery. The device comprises an elongate laparoscopic port within which a laparoscope may be positioned. The distalmost end of the tip is transparent in nature and operatively transitional between a closed configuration and an open, operative configuration, the latter of which causing tissue to be selectively dissected in a layer-by-layer fashion while under the direct vision of the laparoscope disposed therein. The port may further optionally assume an anchor configuration once positioned within the patient to enable the same to remain securely in position during the laparoscopic surgical procedure.

30 Claims, 4 Drawing Sheets

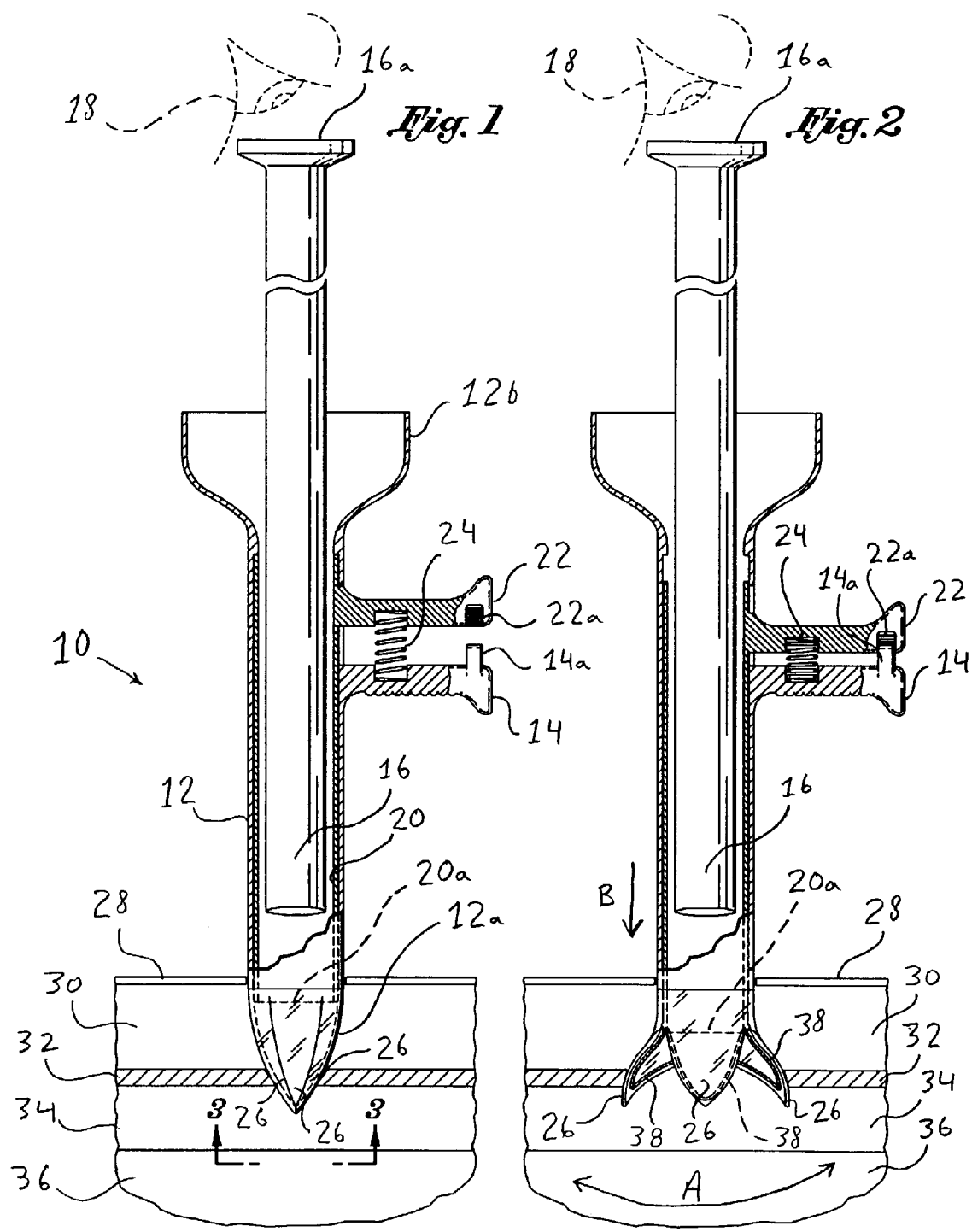

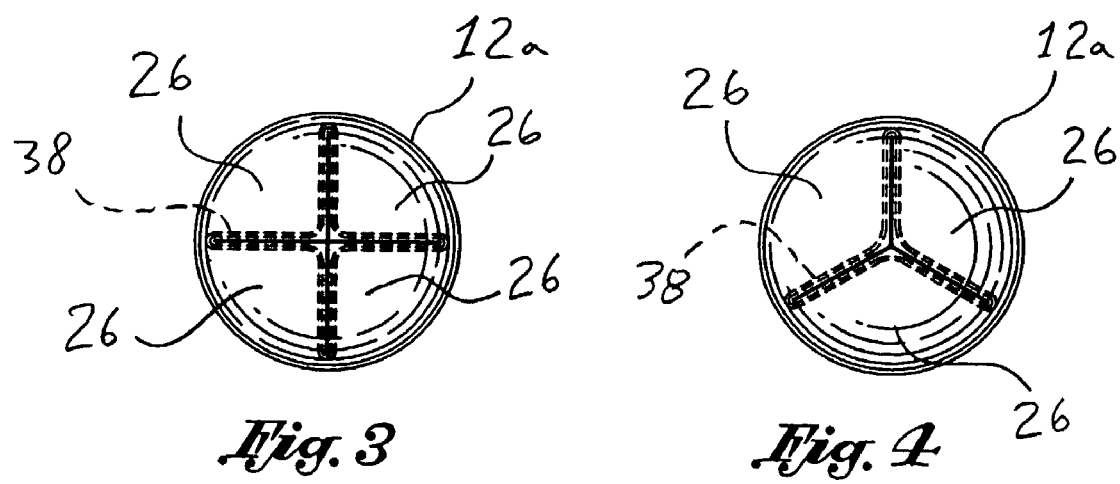
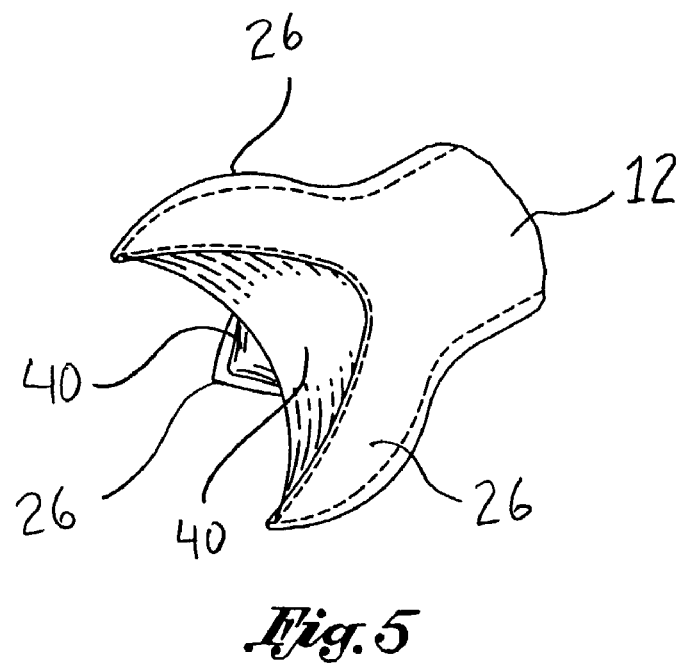

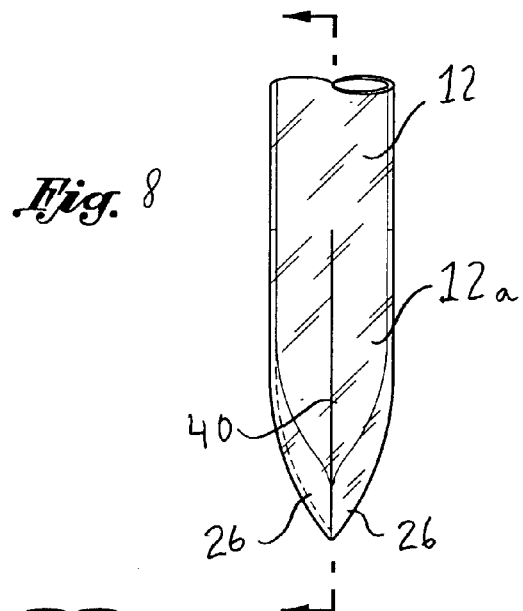
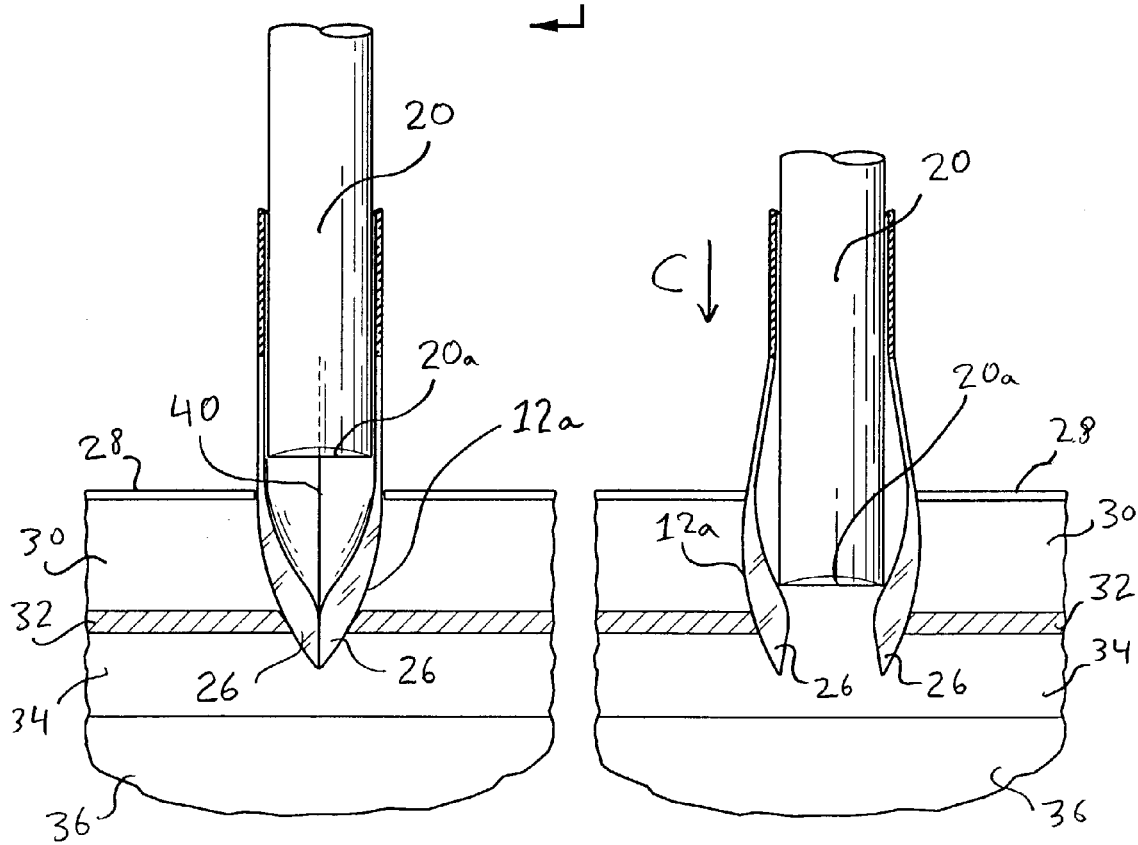
Fig. 8
Fig. 9
Fig. 10

LAPAROSCOPIC DIRECT VISION DISSECTING PORT

CROSS-REFERENCE TO RELATED APPLICATIONS (Not Applicable)

STATEMENT RE: FEDERALLY SPONSORED RESEARCH/DEVELOPMENT (Not Applicable)

BACKGROUND OF THE INVENTION

Laparoscopic surgery is a well-known, widely utilized surgical technique that advantageously reduces patient recovery time due to its minimal tissue damage. Generally, laparoscopic surgery relies upon the formation of one or more puncture wounds through which a body cavity, typically the peritoneal cavity, can be accessed. In this regard, once the peritoneal cavity has been entered, the same is insufflated with carbon dioxide gas, typically to a pressure of approximately 15 mm Hg, followed by the introduction of a laparoscopic port with trocar, which may either be bladed or blunt.

The laparoscopic port is put into the peritoneal cavity followed by the placement of a laparoscope therethrough to thus provide visualization of the cavity thus enabling the surgeon to view the surrounding organs and conduct the surgical procedure. Advantageously, the use of laparoscopic ports through small diameter openings enables the patient to readily heal following surgery, and requires much less recuperation time for the patient as compared to open surgical procedures, which typically deploy long incisions which are generally deemed traumatic to the patient and can involve substantially longer recuperative periods.

Despite its advantages, laparoscopic surgery as currently performed can pose substantial risks to the patient. In this respect, it is widely recognized that entry into the peritoneal cavity during laparoscopic surgery, due to the procedure by which the peritoneal cavity is accessed, can cause serious injury to the abdominal organs, such as the spleen, liver and intestine as well as surrounding blood vessels. This risk is due in large part to the fact that in the unoperated abdomen, most surgeons enter the peritoneal cavity using a Veress needle, which is pushed blindly through the patient's fascia and peritoneum. The peritoneal cavity is then insufflated followed by the introduction of the laparoscopic port with trocar, which also is pushed blindly in the peritoneal cavity. Once positioned therein, a laparoscope is introduced through the port to thus provide visualization within the cavity.

Problematic with such procedure, however, is the fact that the abdomen is entered blindly on two separate occasions, first through the introduction of the Veress needle and second through the laparoscopic port, which can and frequently does injure abdominal organs and surrounding blood vessels.

To the extent laparoscopic surgery is performed upon a patient that has previously undergone an abdominal operation, the preferred surgical practice is to enter the peritoneal cavity under direct vision. In this regard, it is known that when a patient has undergone previous abdominal surgery, the abdominal contents can become adherent to the abdominal wall, making blind placement of a Veress needle or trocar too risky of a technique.

According to such technique, the skin is incised and the subcutaneous tissue dissected until the fascia is encountered. The fascia is then dissected, typically by grasping the fascia with two surgical clamps and incising the fascia sharply followed by successively grasping the subfascial tissue until the peritoneal cavity is entered. Once entered, the laparoscopic port is then placed in the peritoneal cavity under direct vision and the abdomen insufflated with carbon dioxide gas.

Such alternative procedure, however, typically requires a larger skin incision than is typically produced via the use of the Veress needle technique, particularly with respect to obese patients, and is further more prone to gas leakage during surgery, thus requiring constant monitoring and maintenance of adequate insufflation.

In light of such potential complications that can arise via entry into the peritoneal cavity during laparoscopic surgery, attempts have been made to provide means for safely entering into a body cavity utilizing direct visualization. Exemplary of such devices as those disclosed in U.S. Pat. No. 5,441,041, issued to Sauer, et al. on Aug. 15, 1995, entitled Optical Trocar, which utilizes a blade moveable between a non-deployed position and a deployed position to thus allow dissection under visualization of an endoscope. Such device, however, does not allow for any type of spreading of the cut tissue to enable the surgeon to see the next layer of tissue to be entered. As such, dissection is performed without prior visualization thereof.

Other devices that are similar in nature to those disclosed in U.S. Pat. No. 5,441,041 include U.S. Pat. No. 5,720,761, issued to Kalli on Feb. 24, 1998, entitled Visually Directed Trocar and Method; U.S. Pat. No. 5,551,947, issued to Kalli on Sep. 3, 1996, entitled Visually Directed Trocar for Laparoscopic Surgical Procedures and Methods of Using the Same; U.S. Pat. No. 5,609,562, issued to Kalli on Mar. 11, 1997, entitled Visually Directed Trocar and Method; and U.S. Pat. No. 5,385,572, issued to Nobles, et al. on Jan. 31, 1995, entitled Trocar for Endoscopic Surgery; U.S. Pat. No. 5,632,717, issued to Yoon on May 27, 1997, entitled Penetrating Endoscope; U.S. Pat. No. 5,860,996, issued to Urban, et al. on Jan. 19, 1999, entitled Optical Trocar and, the teachings of all of which are expressly incorporated herein by reference.

A similar device attempting to provide direct visualization during entry into a body cavity is shown in U.S. Pat. No. 5,569,291, issued to Privitera, et al., entitled Surgical Penetration and Dissection Instrument, issued on Oct. 29, 1996. Such reference discloses a device for forming an entry into a body cavity performed under direct visualization of an endoscope. The dissecting portion of the device consists of a clear plastic conical tip with elevated dissecting blades that is advanced into the tissue via a twisting motion.

The conical tip, however, is advanced bluntly into the tissue before the same can be identified and, as a consequence, incision of the tissue is performed without prior visualization. In fact, inadvertent entry into an organ cannot be avoided via use of such device, and it is only after the organ is entered (and hence damaged) that such matter can be appraised. Moreover, the use of clear plastic has substandard optical visualization due to optical properties inherent in such material, coupled with the conical shape, such that advancement of the tip fails to provide a clear visualization as the same is advanced through tissue.

Devices similar to those disclosed in U.S. Pat. No. 5,569,921 include U.S. Pat. No. 5,569,292, issues to Scwemberger, et al. on Oct. 29, 1996, entitled Surgical Penetration Instrument with Transparent Blade and Tip Cover; U.S. Pat. No.

5,591,192, issued to Privitera, et al. on Jan. 7, 1997, entitled Surgical Penetration Instrument Including an Imaging Element, issued to Sierocuk, et al. on Apr. 14, 1998, entitled Surgical Dissector and Method of Use; and U.S. Pat. No. 6,206,823, issues to Kolata, et al. on Mar. 27, 2001, entitled Surgical Instrument and Method for Endoscopic Tissue Dissection, the teachings of all of which are incorporated herein by reference.

A further related surgical instrument is disclosed in U.S. Pat. No. 5,354,302, issued to Ko entitled Medical Device and Method for Facilitating Intra-Tissue Visual Observation and Manipulation of Distensible Tissues. Essentially, such device comprises an elongate sheath having a cone-shaped distal end and inner sheath member disposed there within operative to cause the distal end to move tissue away to thus enable tissue to be manipulated and visualized by the inner sheath member. While the cone-shaped distal end is operative to move tissue away such that visualization of tissues and the like can be enhanced, such cone-shaped distal end does not provide any dissection function. Indeed, the flaps of the distal end of the cone member are flimsy in nature and non-reinforced. As such, the same are ill suited for enhancing direct visualization, much less providing any type of dissecting function. Such device is further not designed for use in laparoscopic applications, and in particular a laparoscopic port through which other instruments can be positioned and deployed.

There is thus a substantial need in the art for a system and method that can enable a surgeon to safely enter a body cavity, and in particular the peritoneal cavity, for purposes of performing laparoscopic surgery whereby the surgeon is provided with direct visualization during entry into the cavity such that tissue separation can be visualized and organ and tissue damage can be avoided (i.e., the surgeon can see the tissue prior to dissecting the same). There is additionally need for such a device and system that is capable of forming an entry into a body cavity via a skin incision no greater than that required to admit the introduction of the laparoscopic port and that also preferably forms a tight seal around the port following its introduction such that gas leakage during the laparoscopic surgical procedure is minimized. Still further, there is need for such a system and method which provide for cavity entry without prior insufflation of gas into the cavity but can preferably have a means to insufflate the body cavity following entry, if desired.

BRIEF SUMMARY OF THE INVENTION

The present invention specifically addresses and alleviates the above-identified deficiencies. In this regard, the present invention is directed to a laparoscopic direct vision dissecting port operative to selectively and sequentially dissect through subcutaneous tissue, fascia, pre-peritoneal fat and peritoneum under direct vision of a laparoscope, and thereafter be utilized as a conventional laparoscopic port. According to a preferred embodiment, the invention consists of a laparoscopic port defined by a long tubular section having a proximal end and a distal end, the latter being operative to be inserted through a skin incision made upon the patient. The distal end is formed from a transparent material and is operatively transitional between a first closed configuration wherein said distal end forms a closed, generally conical shape and a second expanded configuration wherein said tip is characterized by a plurality of outwardly extending flap members spreading radially outward relative the elongate tubular section. In a preferred embodiment, the distal end is biased to assume the closed configuration, and may include an additional structure such an elastic recoil or rubber covering to bias the tip to maintain the closed configuration. The flaps formed on the distal end of the laparoscopic port may further preferably be reinforced with wire or a spring mechanism and may be provided with a texturized outer cutter surface to facilitate dissection through tissue as the same is advanced therethrough.

Disposed within the tubular housing of the laparoscopic port is an inner actuator sleeve operatively coupled to a handle mechanism extending from the proximal end of the tubular housing that selectively extends distally within the laparoscopic port when the handle mechanism is actuated to thus cause the distal end of the port to selectively transition between its closed and operative configurations. In this respect, as the actuator sleeve is advanced inwardly toward the closed distal end of the port, the forward axial movement of the actuator causes the flaps of the distal end to extend radially outward, thus causing the tissue surrounding the distal end to selectively spread apart as the distal-most end of the device is advanced into the peritoneal cavity. To help achieve that end, the flaps may be formed to have a gradually increasing wall thickness toward the distal ends thereof to thus enable the same to more readily spread apart as the actuator sleeve is advanced toward the closed distal end of the port.

In use, a conventional laparoscope is positioned within the port and provides the physician with direct vision as each layer of tissue is sequentially spread apart by the advancing distal end of the device. Along these lines, the device will preferably be designed to be utilized with conventional laparoscopic devices and will preferably be made to accommodate either a ten millimeter or five millimeter laparoscope.

To the extent the distal end of the device comes within close proximity to an organ or other anatomical structure sought to be avoided, the surgeon may take appropriate measures to avoid the same. Otherwise, the physician merely advances the distal end of the device, via the sequential spreading of tissue provided by the dissecting distal end of the laparoscopic port, until such time as the peritoneal cavity is entered.

Once entered, the laparoscopic port may be secured into position through the newly dissected incision into the peritoneal cavity. To facilitate the ability of the laparoscopic port to be secured into position within the peritoneal cavity, the same may be accomplished by distally advancing the inner actuator sleeve until such time as the flaps of the distal end of the port extend radially about the opening into the peritoneal cavity. In this respect, it is contemplated that the inner sleeve may be locked into position to facilitate the ability of the distal end of the port to anchor the port into position. Thereafter, as per conventional laparoscopic procedures, the peritoneal cavity may be insufflated with carbon dioxide gas which may be channeled through the laparoscopic port.

It is therefore an object of the present invention to provide a laparoscopic direct vision dissecting port which enables a physician to gain entry into a body cavity, and in particular the peritoneal cavity under direct vision, and thus eliminates the need to blindly enter the same.

Another object of the present invention is to provide a laparoscopic direct vision dissecting port that enables a physician to directly view entry to the peritoneal cavity via a dissection procedure and means of controlling such entry whereby inadvertent dissection of an organ, blood vessel or tissue mass can be avoided or substantially minimized.

Another object of the present invention is to provide a laparoscopic direct vision dissecting port which enables a physician to safely gain entry into the peritoneal cavity under direct vision irrespective as to whether or not the patient has or has not undergone previous abdominal surgery.

Another object of the present invention is to provide a laparoscopic direct vision dissecting port that can enable a laparoscopic port to be placed into position in a manner that simultaneously allows for tissue dissection coupled with laparoscopic port positioning and placement.

Still further objects of the present invention are to provide a laparoscopic direct vision dissecting port that, in addition to substantially minimizing the risk of internal organ injury, is of simple construction, easy to use, relatively inexpensive to manufacture, and can be readily deployed utilizing conventional laparoscopic surgical devices and related techniques.

BRIEF DESCRIPTION OF THE DRAWINGS

These as well as other features of the present invention will become more apparent upon reference to the drawings wherein:

FIG. 1 is a cross-sectional view of a laparoscopic direct vision dissecting port constructed in accordance with the preferred embodiment of the present invention as utilized to gain entry into the peritoneal cavity of a patient, the dissecting port further having disposed therein a laparoscope to enable entry into the peritoneal cavity to be viewed by a physician.

FIG. 2 is a cross-sectional view of the dissecting port of FIG. 1 wherein the distal end thereof is shown in an operative, dissecting configuration.

FIG. 3 is a frontal view of the distal-most tip of the dissecting port of the present invention constructed in accordance with a preferred embodiment.

FIG. 4 is a frontal view of the distal-most tip of the dissecting port of the present invention constructed in accordance with a preferred embodiment.

FIG. 5 is a perspective view of the distal end of the dissecting port of the present invention shown assuming an operative configuration with an optional elastic webbing integrated therein.

FIG. 8 is a perspective view of the distal tip of the dissecting port of the present invention constructed in accordance with another preferred embodiment, the distal tip being shown assuming a neutral, closed configuration.

FIG. 9 is a cross-sectional view taken along line 8—8 of FIG. 8, the distal tip being utilized to gain access into the peritoneal cavity of a patient.

FIG. 10 is the cross-sectional view of FIG. 9 wherein the distal tip is shown assuming an operative, dissecting configuration.

DETAILED DESCRIPTION OF THE INVENTION

Figure 6:
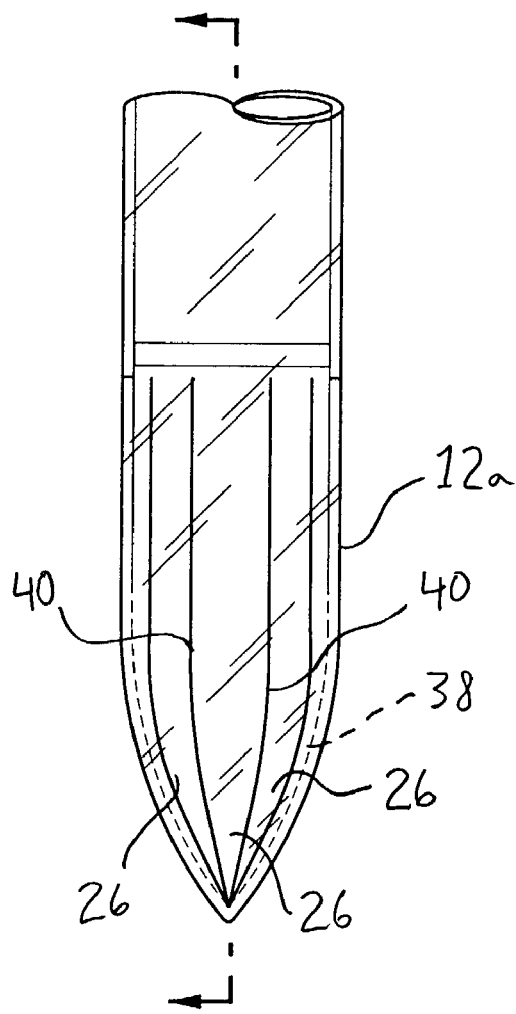
FIG. 6 is a perspective view of the distal end of the dissecting port of the present invention constructed in accordance with another preferred embodiment and assuming a neutral, closed configuration.

The detailed description set forth below is intended as a description of the presently preferred embodiment of the invention, and is not intended to represent the only form in which the present invention may be constructed or utilized. The description sets forth the functions and sequences of steps for constructing and operating the invention. It is to be understood however, that the same or equivalent functions and sequences may be accomplished by different embodiments and that they are also intended to be encompassed within the scope of the invention.

Referring now to the drawings, and initially to FIG. 1, there is shown a cross sectional view of a laparoscopic direct vision dissecting port 10 constructed in accordance with a preferred embodiment of the present invention. As illustrated, the port 10 comprises an elongate tubular housing 12 having a transparent or non-opaque distal end 12a operative to be inserted within an incision formed upon the skin 28 of a patient and a proximal end 12b through which a laparoscope 16 and/or other laparoscopic surgical instruments may be deployed during a conventional laparoscopic surgical procedure. Along these lines, laparoscopes 16 are well-known in the art and are typically provided with an eyepiece 16a on the proximal end thereof to enable the surgeon 18 to view surgical procedures. According to the present invention, however, the laparoscope 16 further enables the surgeon 18 to view the dissecting procedure utilized to gain access into the peritoneal cavity 36 as discussed more fully below. In this regard, the port 10 of the present invention not only is capable of dissecting through tissue under direct vision, but is also capable of serving as a conventional laparoscopic port.

With respect to the dissecting capability of the port 10 of the present invention, there is provided a handle member 14 formed upon the tubular housing 12 and a second handle member 22, the latter coupled with a cylindrical sleeve-like actuator 20 disposed within the lumen of the tubular housing 12 that collectively define a handle capable of being selectively compressed as shown in FIG. 2. Such compressive movement of the handle members 14, 22 facilitates the ability of the device 10 to selectively dissect through tissue, discussed more fully below. In an optional embodiment, a spring member 24 is disposed between handle members 14, 22 to thus cause the handle members 14, 22 to remain in a biased state away from one another. In a further optional embodiment, handle member 14 will have a latch 14a formed thereon and second handle member 22 will have a recess 22a formed thereon for engaging with the latch 14a to thus enable the same to remain in a locked configuration, as shown in FIG. 2. Advantageously, the ability of the handle members 14, 22 to interlock with one another facilitates the ability of the device 10 to become anchored in position, as may e desired when the port is utilized in the performance of a laparoscopic surgical procedure discussed below.

The distal end 12a of the housing 12, in addition to being transparent, is characterized by a plurality of flap members 26 that are operative to assume a first closed configuration, as shown in FIG. 1, whereby the flap members 26 collectively define a closed end having a generally conical shape, and a second, opened and operative configuration, shown in FIG. 2, whereby the flap members 26 radially spread out in the direction indicated by the letter "A". Handle members 14, 22 facilitate the ability of the distal end 12a to selectively transition from the closed configuration depicted in FIG. 1 to the open configuration depicted in FIG. 2. In this regard, by compressing handle members 14, 22, cylindrical actuator 20 is caused to advance distally within the tubular housing 12 such that the distal end 20a of cylindrical actuator 20 internally abuts the flap members 26 such that the same are caused to flare outwardly as shown.

Along these lines, in any embodiment the outward expansion of the flap members 26 causes the tissue surrounding the distal end 12a of the housing 12 to become cut and become spread apart as the distal end 12a of the tubular housing is advanced deeper within the patient. In this regard, the distal end 12a will be positioned through an incision made through skin layer 28 with the flap members 26 being utilized to sequentially cut through subcutaneous fat layer 30, fascia 32, peritoneum 34 and ultimately into the abdominal cavity 36.

To better enable the flap members 26 to expand outwardly, and hence cut through tissue, the same may be formed to have a progressively thicker wall thickness as depicted in FIGS. 8–10. As illustrated in FIG. 8, flap members 26 have wall thickness that gradually increases toward the distal end 12a of the housing. Because the flap members 26 will be formed from a transparent material, the same will not hinder or otherwise obstruct the ability of the laparoscope (not shown) to view the tissues laying just beyond the advancing distal end.

As depicted in FIGS. 9 and 10, in use the distal end 12a of the housing will be inserted into and cut through the various layers of skin and soft tissue 20–34 as described above. To achieve that end, the distal end 20a of cylindrical actuator 20 will be sequentially advanced to the distal end, as illustrated in direction "C" of FIG. 10, to cause flap members 26 to spread apart along slit 40, the latter shown in FIGS. 8 and 9. As will be recognized, due to the increased wall thickness of flap members 26, there is thus provided a more rigid and durable abutment surface upon which distal end 20a may contact. Moreover, such increased wall thickness will advantageously allow flap members 26 to more forcefully and accurately dissect through the various layers of tissue 28–34.

Figure 7:
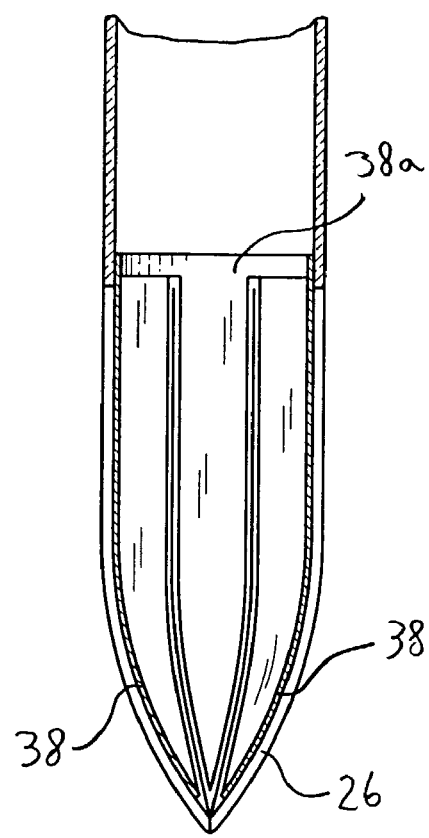
FIG. 7 is a cross-sectional view taken along line 7—7 of FIG. 6.

As will be appreciated by those skilled in the art, the flap members 26 may either be blunt or, alternatively, have a texturized or serrated outer surface (not shown) to facilitate the ability of such flap members 26 to cut through tissue. In this respect, any of a variety of texturized or sharpened objects may be formed upon the flap members 26 to facilitate the ability to cut through and spread apart tissue as the same assume the operative configuration shown in FIGS. 2 and 10. Moreover, as shown in FIGS. 6–7, the flap members 26 may be formed to have a longer length, defined by elongate slits 40, to thus enable the flap members 26 to extend outwardly a greater distance, as may be desired in certain applications.

Along these lines, in order to better facilitate the ability of the flap members 26 of the distal end 12a of the tubular housing 12 to forcefully cut through such layers of tissue, it is contemplated that a wire or spring reinforcement 38 may be embedded within the flap members 26 to thus provide the same with greater structural rigidity. As illustrated in FIGS. 6 and 7, such wire or spring reinforcement 38 may take any of a variety of forms, including a plurality of distally-extending leaf springs emanating from tubular section 38a, which are operative to bias distal end 12a of the housing in the closed configuration as shown.

It is also contemplated that such wire or spring reinforcement 38 may be configured such that the same bias flap member 26 to assume the closed configuration or, alternatively, lock flap members 26 in the opened configuration to thus serve as an anchoring effect. In this regard, it is contemplated that such open configuration may be maintained through the interengagement between latch 14a with recess 22a of the handle members 14, 22, as depicted in FIG. 2. By assuming such open configuration and remaining anchored into position, the port 10 of the present invention can remain securely in position throughout the surgical procedure which is ultimately performed. As will be appreciated by those skilled in the art, by remaining more securely into position, the port enables the physician to more accurately perform a surgical procedure, and/or maintain a more reliable field of view via the laparoscope 16 utilized therewith.

In a further refinement of the present invention, there is shown in FIG. 5 an elastic webbing or sheath 40 which extends between flap members 26 as the same assume the operative configuration as shown. Such elastic sheath 40, which may alternatively take the form of an outer rubber band, rubber sleeve, or the like, advantageously causes the flap members 26 to assume the closed configuration shown in FIG. 1 and further, prevents or substantially minimizes the ability of tissue to be caught between flap members 26 as the same transition between closed and operative configurations. In this regard, elastic sheath 40 serves as a barrier to prevent tissue from getting caught up within the lumen of the tubular housing 12 as the housing 12 is advanced through the tissue. In order to minimize any obstruction of the field of view to be observed by the physician 18, it is contemplated that such sheath 40 will be fabricated from clear or otherwise transparent materials as per the distal end 12a of housing 12 to thus enable the physician to directly visualize the dissection process at all stages thereof.

In this regard, it is essential to the practice of the present invention that at all steps during the procedure the distal end 12a of the tubular housing 12 provide a window to the physician to directly view the dissection process as the flap members 26 selectively transition between closed and operative configurations whereby tissue in and around the distal end is dissected and spread away. As such, at all times the physician is able to see each layer of tissue in advance of its dissection and is able to avoid puncturing or otherwise damaging organs, vessels or other structure. Of further advantage is the fact that as the dissection procedure occurs, the laparoscope is also being caused to form a snug fit about the tissue as the same is cut thereby. As a consequence, the port 10 is capable of being secured within the abdominal cavity 36 in a snug manner that can advantageously eliminate or otherwise substantially minimize any leakage of carbon dioxide gas ultimately used to insufflate the peritoneal cavity.

Along these lines, once the port 10 is advanced into the newly dissected incision into the abdominal cavity 36, the abdominal cavity 36 may be insufflated with carbon dioxide as per conventional laparoscopic surgery. The specific laparoscopic procedure may then be performed as per conventional surgical techniques. To that end it is contemplated that the port 10 will be specifically configured as per conventional ports to have either a 10 mm or 5 mm diameter. It is contemplated, however, that other sizes may be utilized and that the port 10 of the present invention may be configured to be readily integrated into other types of known medical procedures or medical procedures that are later developed.

Additional modifications and improvements of the present invention may also be apparent to those of ordinary skill in the art. For example, it is contemplated that the cylindrical actuator 20 may take any of a variety of forms and may comprise an annular member formed on the distal end of an actuator bar or a retractable wire coupled to wire or spring mechanism 38 such that actuation of the handle members 14, 22 causes wire or spring 38 to cause flap members 26 to transition between closed and operative configurations. Thus, the particular combination of parts in steps described and illustrated herein are intended to represent only certain embodiments of the present invention and is not intended to serve as limitations of alternative devices and methods within the spirit and scope of the invention.

What is claimed is:

1. A laparoscopic direct vision dissecting port comprising:
an elongate tubular housing having proximal and distal ends, said distal end being formed from a non-opaque material and operative to be inserted within an incision on a patient, said housing further being operative to receive and securably hold a laparoscope within the lumen thereof and orient the laparoscope to view through the distal end of said housing;
a plurality of flap members formed upon the distal end of said housing, said flap members being operatively transitional between:
a first closed position wherein said flaps collectively define a generally conical configuration;
an operative configuration wherein said flap members extend radially outward about said distal end of said housing; wherein said flap members include a wire reinforcement formed therein for imparting structural rigidity thereto; and
a handle mechanism formed upon said proximal end of said housing operative to selectively cause said flap members to selectively transition between said closed and operative configurations.

2. The port of claim 1 wherein said wire reinforcement comprises a spring operative to bias the flap members to the closed configuration.

3. The port of claim 1 wherein said flap members include a sharpened cutting surface formed on the surface thereof.

4. The port of claim 1 further comprising an actuator operatively coupled to said handle mechanism and said flap members, said actuator being operative to cause said flap members to selectively transition between said closed and operative configurations when said handle mechanism is actuated.

5. The port of claim 4 wherein said actuator comprises an elongate cylindrical sleeve disposed within said housing and having a distal end in abutment with said flap members, said distal end of said cylindrical sleeve being operative to advance distally within said tubular housing such that said flap members transition from said closed to operative configurations.

6. The port of claim 1 wherein said port further comprises a locking mechanism to cause said flap members to assume said operative configuration.

7. The port of claim 6 wherein said locking members formed upon said handle mechanism of said port.

8. The port of claim 1 wherein said distal end includes at least three flap members formed thereon.

9. The port of claim 1 wherein said distal end includes at least four flap members formed thereon.

10. The port of claim 1 further comprising an elastic sheath formed radially about said plurality of flap members such that said flap members are biased to the closed configuration.

11. The port of claim 1 further comprises an elastic, transparent sheath affixed to said flap members, said sheath being operative to form a covering about the opening of said distal end of said housing when said flap members assume said operative configuration.

12. The port of claim 1 wherein said housing has a diameter of at least five millimeters.

13. The port of claim 1 wherein said housing has a diameter of at least ten millimeters.

14. The port of claim 1 wherein said flap members are formed to have an increased sidewall thickness extending toward said distal ends thereof.

15. The port of claim 1 wherein said wire reinforcement comprises a plurality of distally-extending leaf spring members operative to bias the flap members to the closed configuration.

16. A laparoscopic direct vision dissecting port comprising:
an elongate tubular housing having proximal and distal ends, said distal end being formed from a non-opaque material and operative to be inserted within an incision on a patient, said housing further being operative to receive and securably hold a laparoscope within the lumen thereof and orient the laparoscope to view through the distal end of said housing;
a plurality of flap members formed upon the distal end of said housing, said flap members being operatively transitional between:
i) a first closed position wherein said flaps collectively define a generally conical configuration;
ii) an operative configuration wherein said flap members extend radially outward about said distal end of said housing; and wherein said flap members include a sharpened cutting surface formed on the surface thereof; and
a handle mechanism formed upon said proximal end of said housing operative to selectively cause said flap members to selectively transition between said closed and operative configurations.

17. The port of claim 16 wherein said flap members include a wire reinforcement formed therein for imparting structural rigidity thereto.

18. The port of claim 17 wherein said wire reinforcement comprises a spring operative to bias the flap members to the closed configuration.

19. The port of claim 16 further comprising an actuator operatively coupled to said handle mechanism and said flap members, said actuator being operative to cause said flap members to selectively transition between said closed and operative configurations when said handle mechanism is actuated.

20. The port of claim 19 wherein said actuator comprises an elongate cylindrical sleeve disposed within said housing and having a distal end in abutment with said flap members, said distal end of said cylindrical sleeve being operative to advance distally within said tubular housing such that said flap members transition from said closed to operative configurations.

21. The port of claim 16 wherein said port further comprises a locking mechanism to cause said flap members to assume said operative configuration.

22. The port of claim 21 wherein said locking members formed upon said handle mechanism of said port.

23. The port of claim 16 wherein said distal end includes at least three flap members formed thereon.

24. The port of claim 16 wherein said distal end includes at least four flap members formed thereon.

25. The port of claim 16 further comprising an elastic sheath formed radially about said plurality of flap members such that said flap members are biased to the closed configuration.

26. The port of claim 16 further comprises an elastic, transparent sheath affixed to said flap members, said sheath being operative to form a covering about the opening of said distal end of said housing when said flap members assume said operative configuration.

27. The port of claim 16 wherein said housing has a diameter of at least five millimeters.

28. The port of claim 16 wherein said housing has a diameter of at least ten millimeters.

29. The port of claim 16 wherein said flap members are formed to have an increased sidewall thickness extending toward said distal ends thereof.

30. The port of claim 17 wherein said wire reinforcement comprises a plurality of distally-extending leaf spring members operative to bias the flap members to the closed configuration.

* * * * *